United States Patent
Cappola et al.

(12)

(10) Patent No.: US 6,808,721 B2
(45) Date of Patent: Oct. 26, 2004

(54) METHODS FOR COATING PHARMACEUTICAL CORE TABLETS

(75) Inventors: Michael Cappola, Wilton, CT (US); George W. Gereg, Bethel, CT (US); Susan Way, Danbury, CT (US)

(73) Assignee: Boehringer Ingelheim Pharmaceuticals, Inc., Ridgefield, CT (US)

(*) Notice: Subject to any disclaimer, the term of this patent is extended or adjusted under 35 U.S.C. 154(b) by 84 days.

(21) Appl. No.: 10/282,383

(22) Filed: Oct. 29, 2002

(65) Prior Publication Data

US 2003/0091636 A1 May 15, 2003

Related U.S. Application Data

(62) Division of application No. 09/902,822, filed on Jul. 11, 2001, now Pat. No. 6,565,880.

(51) Int. Cl.[7] .............................. A61K 9/28; A61K 9/30; A61K 9/36
(52) U.S. Cl. .................. 424/474; 424/475; 424/480
(58) Field of Search ................................. 424/474, 475, 424/480, 464, 465, 470, 479, 482

(56) References Cited

U.S. PATENT DOCUMENTS 6,319,921 B1    11/2001   Cirillo et al.
6,462,237 B1 *  10/2002   Gidwani et al. ............ 564/345

* cited by examiner

Primary Examiner—James M. Spear
(74) Attorney, Agent, or Firm—Robert P. Raymond; Anthony P. Bottino; Timothy X. Witkowski

(57) ABSTRACT

A formulation comprising, and process for preparing, improved oral dosage forms of 1-(5-tert-butyl-2-p-tolyl-2H-pyrazol-3-yl)-3-[4-(2-morpholin-4-yl-ethoxy)-naphthalen-1-yl]-urea, a chemical entity with anti-inflammatory properties. Granulation of 1-(5-tert-butyl-2-p-tolyl-2H-pyrazol-3-yl)-3-[4-(2-morpholin-4-yl-ethoxy)-naphthalen-1-yl]-urea within specified ranges provides improved dissolution of 1-(5-tert-butyl-2-p-tolyl-2H-pyrazol-3-yl)-3-[4-(2-morpholin-4-yl-ethoxy)-naphthalen-1-yl]-urea and oral bioavailability, as well as content uniformity. Incorporation into the formulation of an aqueous soluble inclusion compound capable of forming a complex with 1-(5-tert-butyl-2-p-tolyl-2H-pyrazol-3-yl)-3-[4-(2-morpholin-4-yl-ethoxy)-naphthalen-1-yl]-urea, such as beta-cyclodextrin provides enhanced stability of 1-(5-tert-butyl-2-p-tolyl-2H-pyrazol-3-yl)-3-[4-(2-morpholin-4-yl-ethoxy)-naphthalen-1-yl]-urea, in particular in highly ionic environments. Chipping and disintegration of tablets containing more than about 10% betacyclodextrin can be prevented by applying a polymeric coat to the surface of the tablet at a temperature below 40° C.

12 Claims, 5 Drawing Sheets

METHODS FOR COATING PHARMACEUTICAL CORE TABLETS

RELATED APPLICATION DATA

This application is a divisional case of U.S. application Ser. No. 09/902,822, filed Jul. 11, 2001, now U.S. Pat. No. 6,565,880.

BACKGROUND OF THE INVENTION

1. Field of the Invention

The present invention relates to unique oral dosage formulations of 1-(5-tert-butyl-2-p-tolyl-2H-pyrazol-3-yl)-3-[4-(2-morpholin-4-yl-ethoxy)-naphthalen-1-yl]-urea, a pharmacological agent exhibiting novel anti-inflammatory activity. More particularly, the present invention relates to oral dosage formulations of 1-(5-tert-butyl-2-p-tolyl-2H-pyrazol-3-yl)-3-[4-(2-morpholin-4-yl-ethoxy)-naphthalen-1-yl]-urea that provide enhanced stability of the compound in ionic environments, improved solubility, and/or improved oral bioavailability, and are produced using unique process conditions.

2. Background of the Related Art 1-(5-tert-butyl-2-p-tolyl-2H-pyrazol-3-yl)-3-[4-(2-morpholin-4-yl-ethoxy)-naphthalen-1-yl]-urea (hereinafter, "BIRB 796") is disclosed in commonly assigned co-pending PCT Application No. PCT/US99/29165, and U.S. Pat. No. 6,319,921, herein incorporated by reference, as possessing unexpectedly significant inhibitory activity with respect to proinflammatory cytokines, such as tumor necrosis factor (TNF) and interleukin-1 (IL-1).

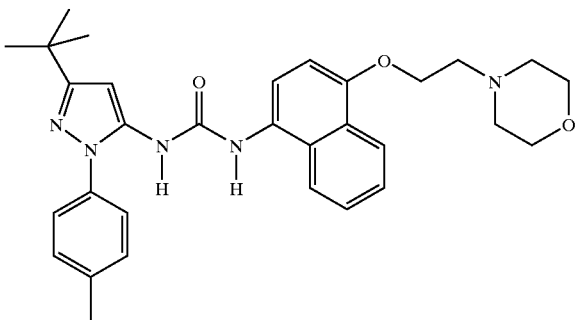

BIRB 796 has implications for the treatment of numerous disease states including arthritis, psoriasis and Crohn's disease. While having many advantageous pharmacological properties, BIRB 796 has been found to possess certain less than desirable pharmaceutical properties, including poor aqueous solubility, poor powder flow properties, and a tendency to discolor in the presence of light.

At least seven polymorphs of BIRB 796 have been isolated (the melt point of the drug is about 152° C. and the pKa about 6.1). The polymorphs generally exist in the form of elongated needles. BIRB 796 is relatively poorly soluble in physiological environments. The solubility of polymorphic BIRB 796 drug substance (Form IV) has been determined to be about 0.5 ug/ml at pH 7.4 and about 10 mg/ml at pH 2.0.

BIRB 796 may be administered by the many routes of administration known in the art, including, but not limited to, orally, intravenously, intraperitoneally, intramuscularly, subcutaneously, bucally, rectally, aurally, ocularly, transdermally, etc. A preferred route of administration is oral administration by way of, for example, tablets, capsules, caplets, troches, lozenges, powder, cachets, solutions and suspensions. Core tablets may be prepared by addition of excipient, binder, disintegrant, lubricant and so on, as would be understood by one of ordinary skill in the art. Core tablets containing BIRB 796 may be subjected to surface coating with a main coating agent such as, but not limited to, hydroxypropylmethylcellulose, hydroxymethylcellulose, hydroxypropyl cellulose and the like. Formulations have been prepared which deliver doses from 0.5 mg to 300 mg.

The present inventors have recently discovered that the solubility of BIRB 796 is adversely diminished when in the presence of ionic solutions. Increasing ionic strength has been found to result in an overall decrease in the dissolution of BIRB 796. As the various parts of the human (and other mammalian) intestinal tract show considerable variability in ionic strength (typically ranging from I=0.15–0.40 M), and as the ionic strength of the intestinal tract may be significantly affected by intake of certain pharmaceutical products and foodstuffs, this variability of the solubility of BIRB 796 with ionic strength may have significant adverse impacts on the overall bioavailability of BIRB 796.

BIRB 796 formulations have also been discovered to be plagued with less than desirable adherency characteristics. Formulations containing BIRB 796 have been found to suffer from the tendency of materials to stick to compression dies and/or punch faces, as well as to stick to powder conduits, filling tubes, and other processing chambers. Within conventional ranges, increases in the amount of lubricant in the formulation have not been found to be adequate to resolve the problem.

There is a need therefore for formulations of BIRB 796 with improved solubility and diminished adherency characteristics, which provide better oral bioavailability of the drug as well as allow for efficient preparation of dosage forms.

SUMMARY OF THE INVENTION

The present invention discloses formulations of BIRB 796, and processes for manufacturing such BIRB 796 formulations, that provide for improved solubilization and/or bioavailability of BIRB 796, and which display improved flow characteristics. In particular, advantageous oral dosage formulations of BIRB 796 are provided.

It has been discovered by the present inventors that the flow properties of BIRB 796 drug substance may be significantly improved (adherence to surfaces reduced), by granulation of the material followed by milling of the dried granules in such a manner so as to form a granular composition of BIRB 796 within a defined range of granule sizes—such that the portion of granules which do not pass through a 1000 micron sieve do not account for more than about 5 percent by weight of the total granules, the amount that do not pass through a 250 micron sieve does not account for more than about 60 percent by weight, and the portion of granules which pass through a 63 micron sieve do not account for more than about 20 percent by weight. Such granular compositions of BIRB 796 have been obtained using a cone mill set at various rpms with a 1000 micron rasp or grate screen. Manual milling through a 1000 micron screen, followed by a 700 micron screen has also been found capable of producing such acceptable sieve patterns.

Surprisingly, it has been determined by the present inventor that BIRB 796 solubility is peculiarly affected by the ionicity of its attendant milieu. In particular, aqueous solubility of BIRB 796 has been found to significantly decrease as the ionic strength of its milieu increases. Decreased dissolution has been found to affect overall bioavailability of drugs.

Presented with numerous possibilities for protecting BIRB 796 from ionic interaction, the present inventor has discovered (after numerous failed attempts) a relatively cheap and effective alteration in formulation that may be made that significantly improves BIRB 796 dissolution in ionic solutions. Such improved formulation includes a pharmaceutically non-toxic, aqueous-soluble, inclusion compound (preferably polymeric in form) that is capable of forming a complex with BIRB 796 via manufacture by wet or dry granulation and in its aqueous state so as to protect BIRB 796 from interaction with ionic species. By inclusion compound it is meant a compound capable of forming a cage structure with an unrelated molecule so as to form a well-defined addition structure (the cage structure being formed by one or more molecules of inclusion compound). A preferred inclusion compound of the present invention contains amylose moieties. A particularly preferred inclusion compound is cyclodextrin. A particularly preferred cyclodextrin is β-cyclodextrin.

When employing beta-cyclodextrin in combination with BIRB 796 to protect against ion-induced diminishment of BIRB 796 solubilization, it is preferred that the beta-cyclodextrin:BIRB 796 weight ratio be at least about 1, more preferably to be at least about 2, and yet more preferably to be at least about 3. Such mixtures have been found to significantly enhance the dissolution of BIRB 796 in aqueous solutions, with the higher beta-cyclodextrin composition generally providing a better overall effect.

Unexpectedly, it further has been discovered that standard techniques for application of coating material to core tablets need to be altered when the core tablet contains significant amounts of a cyclodextrin (greater than about 10%). While coatings are conventionally applied at temperatures of 40° C. or above, it has been found that when a compression (i.e. tablets and the like) contains cyclodextrins that the coating temperature must be kept below 40° C. in order to prevent chipping and ultimately disintegration of the compression. Such chipping and disintegration problem is particularly noted when the core tablet contains substantial amounts of cyclodextrin ($\geq$ about 40%). In particular, coatings applied to compressions (such as core tablets) containing beta-cyclodextrin need to be applied at temperatures below 40° C., more preferably below 39° C., temperatures above 40° C. causing chipping and disintegration of the compression.

The addition of cyclodextrin inclusion compounds to the BIRB 796 oral formulation was seen to improve the average total plasma concentration of BIRB 796 (in dogs) over a twelve hour period ($AUC_{0-12}$), as well as the maximum plasma concentration ($C_{max}$) attained as compared to formulations containing lactose. The time to maximum concentration ($T_{max}$) was also seen to be reduced as compared to lactose formulations lacking cyclodextrin.

One aspect of the present invention consists of a pharmaceutical oral dosage form comprsing: (a) a pharmaceutically effective dose of BIRB 796; and (b) a pharmaceutically non-toxic amount of an aqueous soluble inclusion compound that is capable of forming a complex with BIRB 796 in its aqueous state so as to substantially protect BIRB 796 from interaction with ionic species.

In another embodiment of the present invention, there is disclosed pharmaceutical tablet comprising: (a) a homogenous core comprising granulated BIRB 796 and a cyclodextrin; and (b) a coating completely covering said homogenous core which comprises any suitable coating, and preferably a water dispersible pharmaceutically-acceptable polymer coating, or the like.

In yet another embodiment of the present invention, there is disclosed a pharmaceutical tablet comprising: (a) between about 0.1 to about 35% by weight granulated BIRB 796; (b) between about 25 to about 50% by weight binding agent; (c) between about 3 to about 40% by weight disintegrant; and (d) between about 25 to about 60% by weight soluble granulation aid.

BRIEF DESCRIPTION OF THE DRAWINGS

The above description, as well as further objects, features and advantages of the present invention will be more fully understood with reference to the following detailed description when taken in conjunction with the accompanying drawings, wherein.

DETAILED DESCRIPTION OF THE INVENTION

Figure 1:
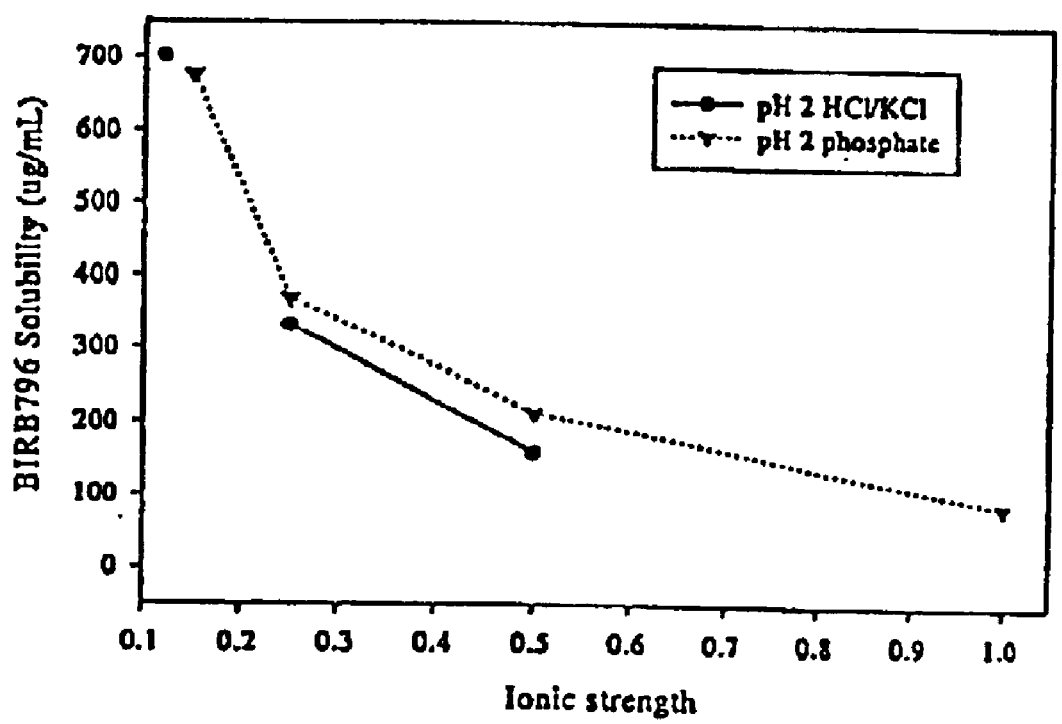
FIG. 1 is a graph of the solubility ($\mu$g/ml) of BIRB 796 versus ionic strength at pH 2 of an aqueous HCl/KCl solution (lower curve) and aqueous phosphate solution (upper curve).

The present invention overcomes many of the problems associated with the less than desirable solubility and handling characteristics of BIRB 796. The present invention provides novel formulations of BIRB 796 that improve the solubility and bioavailabilty of BIRB 796 in oral dosage forms, as well as its powder flow properties related to manufacture. While the present specification mentions BIRB796, it is also contemplated that closely related analogs, homologs, positional isomers, tautomers and metabolites of BIRB 796 such as those found in U.S. application Ser. No. 09/484,638 are also within the scope of the invention. U.S. application Ser. No. 09/484,638 and all references cited in this application are incorporated herein by reference in their entirety.

Dissolution performance is an important consideration in any oral formulation. Formulation, however, must also take into account the need for economically practicable methods to produce a wide range of oral potencies that are physiochemically stable. Further, components of any formulation must possess satisfactory processing properties. As a drug substance, BIRB 796 is a fine powder with poor flow characteristics making it less than desirable with respect to processing. BIRB 796 is also a poorly soluble crystalline material. The present invention provides for the economical production and processing of physiochemically stable oral dosage forms of BIRB 796 with improved bioavailability.

In order to improve both the flow characteristics and dissolution rate of BIRB 796, both wet and dry granulation of BIRB 796 crystals were investigated and both found successful. Due to enhanced performance, wet granulation was chosen. Wet granulations (after drying) were subsequently milled in an oscillating mill with a 700 micron screen. It was found that formulations incorporating such granules had the tendency to stick to the tablet die/punch and flow tubes. Increases in lubricant level in the formulation within conventional tablet lubricant ranges, from 0.75% to 0.125%, was not sufficient to correct the problem.

Cone milling of the BIRB 796 granules prepared by wet granulation was subsequently attempted in order to reduce dusting and to gain more control over the homogeneity of the granules produced. A cone mill with various micron rasp or grate screens was employed. It was found that a cone mill having a raised area for grating the granulation significantly reduced dusting. The rotor speed of the mill and rasp screen size were repeatedly adjusted to produce different particle size distributions. Such granulations were then tested to determine acceptable sieve patterns with respect to granulations exhibiting good solubility, good bulk flow, acceptable content uniformity and no evidence of powder or tablet sticking.

While several rasp screen mesh sizes were investigated, with adjustment of rotor speed, cone milling with a 1000 micron rasp screen was found capable of producing granules of appropriate particle size distribution insuring good content uniformity. This devised procedure insured acceptable dissolution results with BIRB 796 as well as resulted in a material which did not suffer from sticking problems.

BIRB 796 granules having a defined distribution range of granule sizes were found to provide both substantial improvements in BIRB 796 uniformity as well as to possess insubstantial sticking properties with respect to process apparatus materials. Acceptable sieve patterns suggest that to effectuate pharmaceutically acceptable improvement in content uniformity, the portion of granules that do not pass through a 1000 micron sieve should not account for more than about 5 percent by weight of the total granules, the amount that do not pass through a 250 micron sieve should not account for more than about 60 percent by weight, and the portion of granules which pass through a 63 micron sieve should not account for more than about 20 percent by weight. Such acceptable sieve patterns does not take into account drug dusting due to inappropriate milling techniques (drug dusting can not be measured by sieve analysis as the small particles mostly likely are in the 1–5 micron size and adhere to the larger granules by static charge). Representative examples of acceptable sieve patterns are set forth in Table 1 below:

TABLE 1

Acceptable Sieve Patterns For Granulated BIRB 796

| Sieve Diameter | Acceptable Sieve Patterns (Percent of Total Particles) | | |
|---|---|---|---|
| (microns) | Sample 1 | Sample 2 | Sample 3 |
| 1000 | 2.3 | 0.34 | 3.0 |
| 500 | 30 | 18 | 16 |
| 250 | 25 | 26 | 39 |
| 125 | 22 | 23 | 24 |
| 63 | 13 | 20 | 13 |
| <63 | 7 | 13 | 6 |

As would be understood by one of ordinary skill in the art, rotor speeds (as well as the duration of milling) useful for producing such acceptable distributions differ substantially between models of cone mills, as well as with the rasp screen size selected. Such selections are well within the skill of one of ordinary skill in the art. Of course, other milling methods known in the art may also be used to produce such a granule distribution. For example, successive manual milling through a 1000 micron and then 700 screen was used to produce BIRB 796 granule distributions coming within the above defined acceptable sieve pattern range. Wet milling of granulation prior to drying is another technique that may be utilized to produce such granule distribution.

Figure 2:
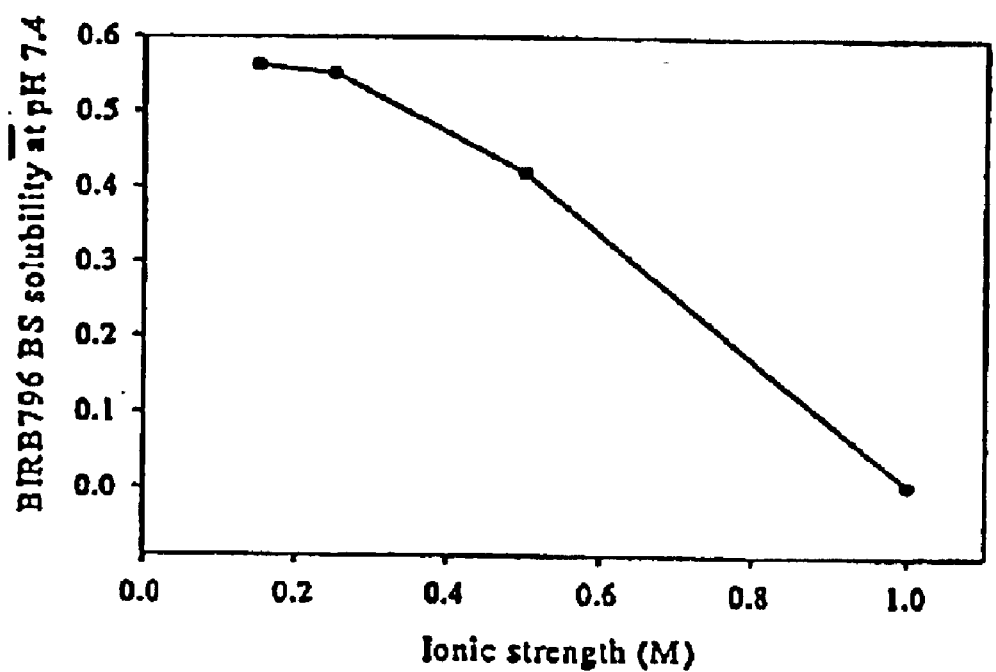
FIG. 2 is a graph of the solubility ($\mu$g/ml) of BIRB 796 versus ionic strength at pH 7.4 of an aqueous phosphate solution.

Unexpectedly, the present inventors have discovered that BIRB 796 solubility is adversely affected by highly ionic aqueous solutions. FIG. 1 demonstrates that with respect to a HCl/KCl aqueous solution at pH 2 (upper curve), and an aqueous solution containing phosphate (lower curve), as the ionic strength of the solution increases the solubility of BIRB 796 decreases. Similarly, as shown in FIG. 2, the solubility of BIRB 796 in phosphate buffer at pH 7.4 decreases nearly linearly as the ionic strength of the solution increases. The decrease in BIRB 796 solubility therefore is observed at physiological relevant pH values. The decrease in aqueous solubility of the drug may have profound effects on dosage form performance.

The present inventors have discovered that by incorporating a pharmaceutically non-toxic, aqueous-soluble inclusion compound (preferably polymeric in form) that is capable of forming a complex with BIRB 796 in its aqueous state (and preferably also in its solid state), that the solubility of BIRB 796 can be significantly enhanced, in particular in highly ionic solutions. Among the numerous inclusion compound-BIRB 796 combinations attempted, it has been discovered that compounds comprising amylose moieties are unexpectedly useful in aiding dissolution of BIRB 796. A particularly preferred inclusion compound is cyclodextrin. Among the cyclodextrins employed, β-cyclodextrin has been found to be particularly advantageous.

It is preferred (but not required) that beta-cyclodextrin be incorporated into a BIRB formulation in an amount (weight basis) at least about that of BIRB 796, more preferably approximately twice that of BIRB 796, and yet more preferably approximately three times that of BIRB 796. When beta-cyclodextrin is used with BIRB 796 to form tablets, it has been found that a generally lower compressional force (than that with matching lactose formulas) should be used to assure tablet disintegration.

In order to evaluate the effect of ionic strength on the dissolution of BIRB 796 from tablets with/without aqueous soluble BIRB 796 inclusion compounds, studies were conducted with formulations containing lactose and different amounts of beta-cyclodextrin.

Figure 3A:
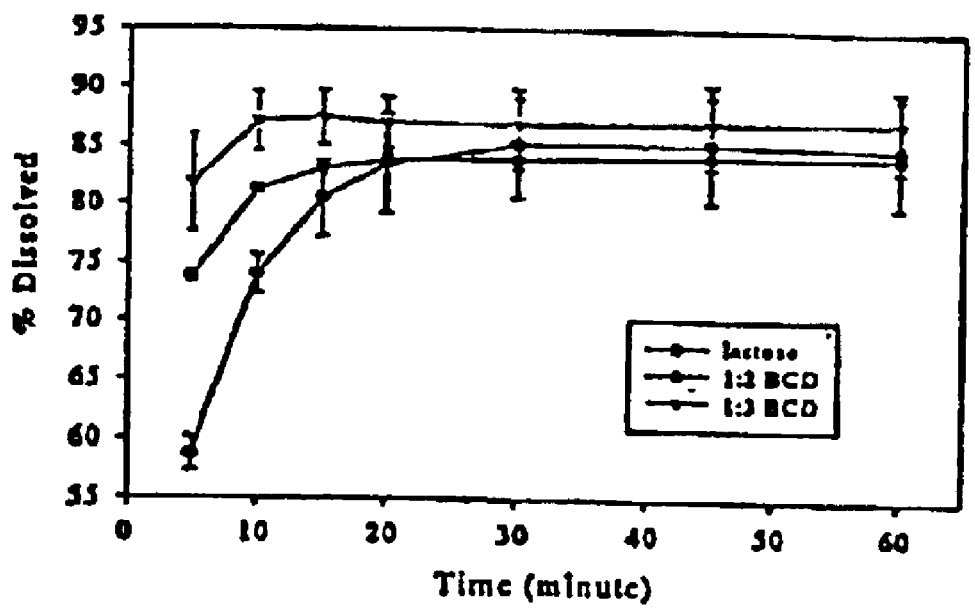
FIG. 3a is a graph of the percentage of 100 mg of BIRB 796 dissolved in an aqueous phosphate solution at pH 2 (37° C.) at ionic strength I=0.25 for formulations containing 3.7 parts lactose to 1 part BIRB 796 (lower curve), 2 parts beta-cyclodextrin to 1 part BIRB 796 and 1.7 parts lactose (middle curve), and 3 parts beta-cyclodextrin to 1 part BIRB 796 and 0.7 parts lactose (uppermost curve).
Figure 3B:
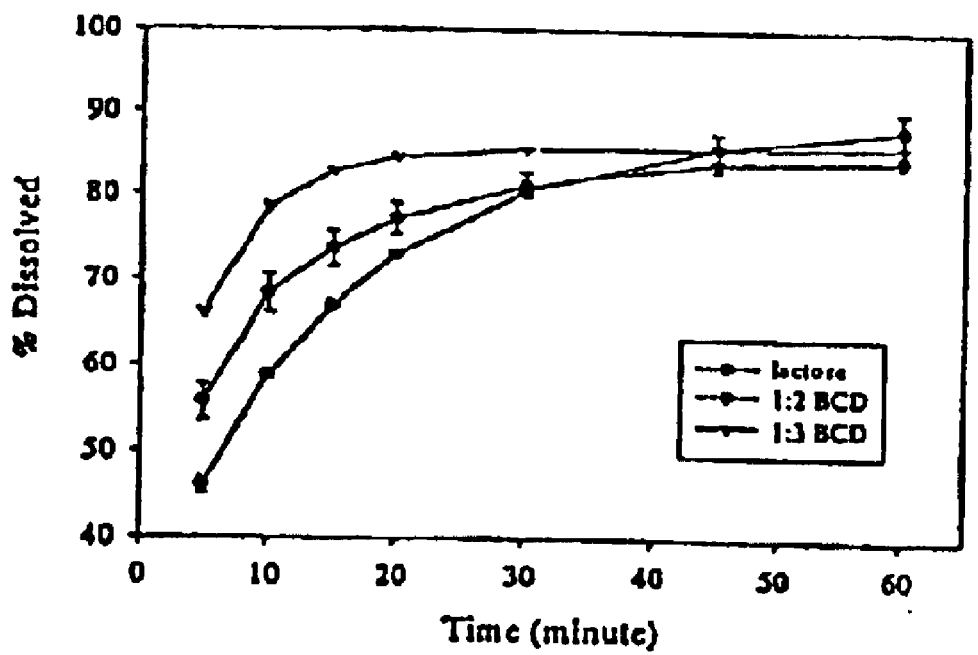
FIG. 3b is a graph of the percentage of 100 mg of BIRB 796 dissolved in an aqueous phosphate solution at pH 2 (37° C.) at ionic strength I=0.50 for formulations containing 3.7 parts lactose to 1 part BIRB 796 (lower curve), 2 parts beta-cyclodextrin to 1 part BIRB 796 and 1.7 parts lactose (middle curve), and 3 parts beta-cyclodextrin to 1 part BIRB 796 and 0.7 parts lactose (uppermost curve).

FIGS. 3a and 3b illustrate in graphic form the effect of beta-cyclodextrin on BIRB 796 solubility (as a percent of 100 mg of BIRB 796 dissolved) in an aqueous phosphate solution at pH 2 (37° C.) at ionic strengths I=0.25 M (FIG. 3a) and I=0.50 M (FIG. 3b), for formulations containing 3.7 parts lactose to 1 part BIRB 796 (lower curve), 2 parts beta-cyclodextrin (BCD) to 1 part BIRB 796 and 1.7 parts lactose (middle curve), and 3 parts beta-cyclodextrin to 1 part BIRB 796 and 0.7 parts lactose (uppermost curve). The data evidences that in all cases dissolution was lowest with the lactose formulation as compared to formulations containing cyclodextrin (1(BIRB 796):3 (BCD)>1:2>lactose) at both ionic strengths. Increasing ionic strength resulted in an overall decrease in the dissolution of the tablets. It is hypothesized that beta-cyclodextrin reduces the impact of the ionic strength of the medium by complexing the BIRB 796 such that it does not interact with the ionic species.

Figure 4A:
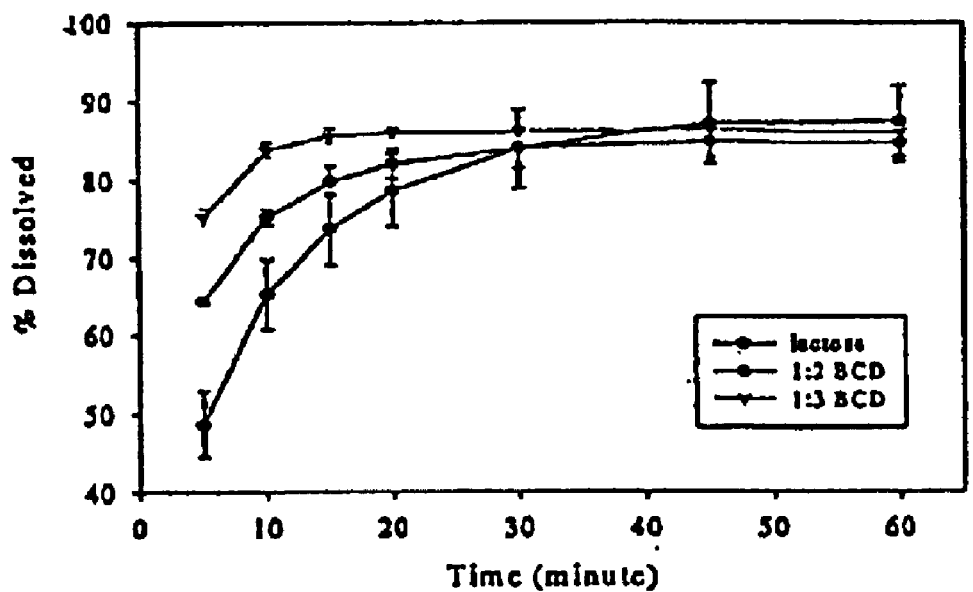
FIG. 4a is a graph of the percentage of 100 mg of BIRB 796 dissolved in an aqueous HCl/KCl solution at pH 2 (37° C.) at ionic strength I=0.25 for formulations containing 3.7 parts lactose to 1 part BIRB 796 (lower curve), 2 parts beta-cyclodextrin to 1 part BIRB 796 and 1.7 parts lactose (middle curve), and 3 parts beta-cyclodextrin to 1 part BIRB 796 and 0.7 parts lactose (uppermost curve).
Figure 4B:
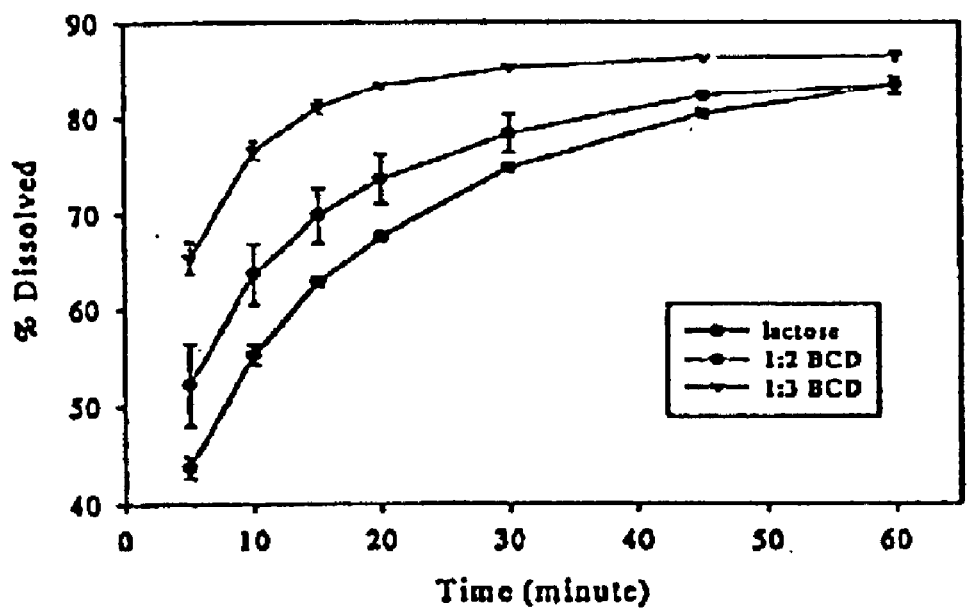
FIG. 4b is a graph of the percentage of 100 mg of BIRB 796 dissolved in an aqueous HCl/KCl solution at pH 2 (37° C.) at ionic strength I=0.50 for formulations containing 3.7 parts lactose to 1 part BIRB 796 (lower curve), 2 parts beta-cyclodextrin to 1 part BIRB 796 and 1.7 parts lactose (middle curve), and 3 parts beta-cyclodextrin to 1 part BIRB 796 and 0.7 parts lactose (uppermost curve).

FIGS. 4a and 4b illustrate in graphic form the effect of beta-cyclodextrin on the dissolution of a 100 mg BIRB 796 tablet dissolved in an aqueous HCl/KCl solution at pH 2 (37° C.) at ionic strengths I=0.25 M (FIG. 4a) and I=0.05 M (FIG. 4b) for formulations containing 3.7 parts lactose to 1 part BIRB 796 (lower curve), 2 parts beta-cyclodextrin to 1 part BIRB 796 and 1.7 parts lactose (middle curve), and 3 parts beta-cyclodextrin to 1 part BIRB 796 and 0.7 parts lactose (uppermost curve). The same trends in dissolution behavior as seen with the aqueous phosphate solution of FIGS. 3a and 3b were observed with the HCl/KCl aqueous solution (pH 2) with rank order of dissolution being: three parts beta-cyclodextrin to one part BIRB 796 (uppermost curve)>two parts beta-cyclodextrin to one part BIRB 796 (middle curve)>3.7 parts lactose to one part BIRB 796 (lower curve). As in the aqueous phosphate solution of FIGS. 3a and 3b, the maximum amount dissolved in 60 minutes was not impacted significantly by ionic strength for any of the formulations.

The effect of beta-cyclodextrin on BIRB 796 solubility (as a percent of 100 mg of BIRB 796 dissolved) in an aqueous phosphate solution at pH 2 (37° C.) and an aqueous HCl/KCl solution at pH 2 (37° C.) was also determined at the relatively low ionic strength I=0.12 M. With respect to the aqueous phosphate solution, beta-cyclodextrin was found overall to improve dissolution over a sixty-minute time frame, although statistical significance ($p<0.05$) was not discerned at any one point. With respect to the aqueous HCl/KCl solution, on the other hand, while beta-cyclodextrin was found to improve dissolution over most of the first ten minutes after initial exposure of the tablet to the solution, beta-cyclodextrin incorporation was seen to reduce dissolution of the BIRB 796 for the next 50 minutes. It is believed that such decrease is artifactual due to a common ion effect (chloride) as ionic strength was controlled by addition of NaCl in all cases (such effect being substantially unimportant at the higher ionic strengths tested in the aqueous HCl/KCl solutions).

The initial rate of dissolution (mg/min) as a function of ionic strength for the representative solutions and formulations tested is set forth below in Table 2:

TABLE 2

Effect of ionic strength on initial rates of dissolution of BIRB 796 tablets (100 mg)

| Dissolution Medium | Tablet Formulation | Initial Rate of Dissolution (mg/min) As a Function of Ionic Strength | | |
|---|---|---|---|---|
| | | 0.12M | 0.25M | 0.5M |
| phosphate, pH 2 | Lactose | 17.05 | 11.75 | 9.16 |
| | 1:2 BCD | 17.24 | 14.74 | 11.09 |
| | 1:3 BCD | 17.19 | 16.32 | 13.18 |
| HCl/KCl, pH 2 | Lactose | 13.33 | 9.74 | 8.72 |
| | 1:2 BCD | 15.31 | 12.85 | 10.45 |
| | 1:3 BCD | 17.07 | 15.00 | 13.07 |

Such data suggests that beta-cyclodextrin affords protection from bulk solvent properties that may adversely effect on dosage form performance, and adversely impact on overall bioavailability as various parts of the intestinal tract show considerable variability of ionic strength, ranging from I=0.15 to 0.40 M.

To evaluate differences in in vivo performance of BIRB 796-lactose test formulations versus BIRB 796-beta-cyclodextrin test formulations, a relative bioavailability study was conducted in dogs. Six dogs (approximately 10 kilograms each) were dosed in a crossover fashion with 100 mg test tablets containing either lactose or beta-cyclodextrin. The composition of the tablets used in the study are set forth below in Table 3:

TABLE 3

Composition of Tablets Evaluated in Dog Bioavailability Studies

| | Amount (mg) | |
|---|---|---|
| Component | Lactose Formulation | Beta-Cyclodextrin Formulation |
| BIRB 796 | 100.0 | 100.0 |
| Beta-cyclodextrin | 0.0 | 200.0 |
| Microcrystalline Cellulose | 225.0 | 225.0 |
| Lactose | 365.0 | 165.0 |
| Colloidal Silicon Dioxide | 7.5 | 7.5 |
| Pregelatinized Starch | 30.0 | 30.0 |
| Sodium Starch Glycolate | 15.0 | 15.0 |
| Magnesium Stearate | 7.5 | 7.5 |
| Total tablet weight (mg) | 750.0 | 750.0 |

Figure 5:
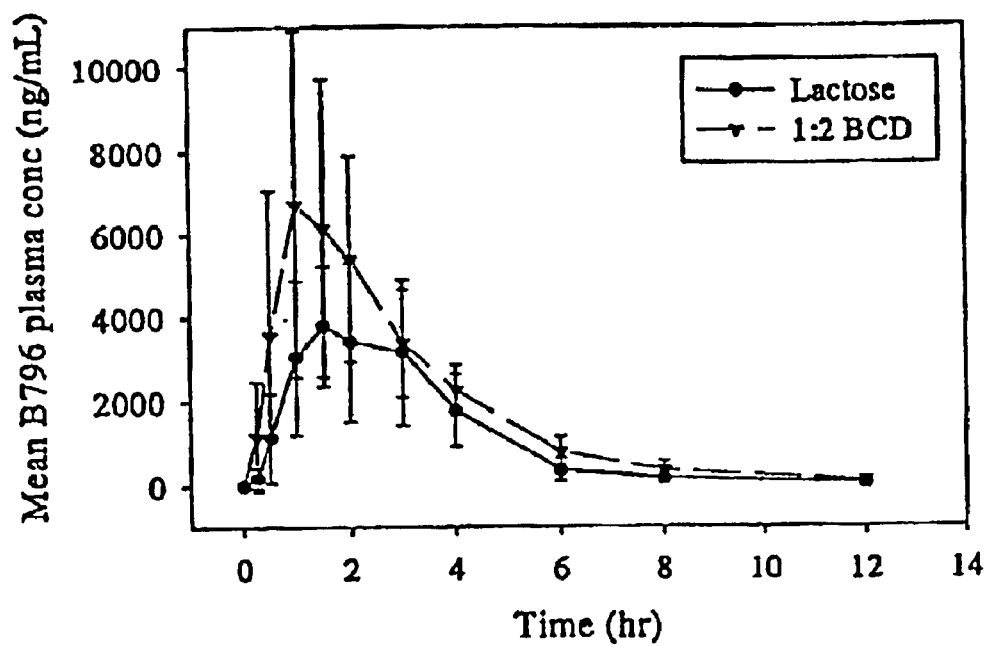
FIG. 5 is a graph of mean BIRB 796 plasma concentration after oral administration of a 100 mg BIRB 796 tablet containing 1 part BIRB 796 to 3.7 parts lactose (lower curve), and administration of a 100 mg BIRB 796 tablet containing 1 part BIRB 796 to 2 parts beta-cyclodextrin and 1.7 parts of lactose (upper curve).

Blood samples were taken over time to determine pharmacokinetic parameters. FIG. 5 sets for in graphical form mean BIRB 796 plasma concentration after oral administration of a 100 mg BIRB 796 tablet containing 1 part BIRB 796 to 3.7 parts lactose (lower curve), and administration of a 100 mg BIRB 796 tablet containing 1 part BIRB 796 to 2 parts beta-cyclodextrin to 1.7 parts lactose (upper curve).

The addition of beta-cyclodextrin to the BIRB 796 oral formulation was seen to improve the average plasma concentration of BIRB 796 over a twelve hour period ($AUC_{0-12}$) (by a factor of about 1.58), as well as the maximum plasma concentration ($C_{max}$) (by a factor of about 1.62) attained as compared to lactose. The time to maximum concentration ($T_{max}$) was also seen to be reduced as compared to lactose formulations (i.e., lacking cyclodextrin). Measured values for such parameters are set forth in Table 4 below:

TABLE 4

BIRB 796 Pharmacokinetic Parameters Following Oral Administration To Dogs

| Parameter | Formulation | |
|---|---|---|
| | Lactose | 1:2 BCD |
| $AUC_{0-12} \pm SD$ (ng · hr/mL) | 13586 ± 4666 | 21537 ± 7426 |
| $C_{max}$ (ng/mL) | 4718 | 7647 |
| $T_{max}$ (hr) | 1.92 | 1.67 |

While beta-cyclodextrin has been seen to offer unexpected improvement in BIRB 796 dissolution and bioavailability, surprisingly it noted during experimental work that core tablets containing cyclodextrins could not be coated under the same conditions as lactose-based formulas, due to tablet chipping and disintegration when the coating was applied. After investigating several possible parameters which might relate to such effect, it was determined that temperature is a critical control variable. Coating was able to be performed using the same coating solution/process/equipment as that for lactose-based formulas only when low temperature coating was performed. As product temperatures moved above 40° C. during coating, tablets containing substantial amounts of beta-cyclodextrin ($\geq$ about 40%) were seen to disintegrate to the point until no tablet integrity was left. Product temperatures above 40° C. especially with larger tablets (e.g., 12 mm tablets) create chipping and crumbling problems. However, when process temperatures were less than about 40° C., more preferably less than about 39° C., acceptably coated tablets could be produced, displaying adequate coating hardness and thickness. Preferred coating temperatures overcoming in most cases such problems are: (1) inlet air temperature between about 30 to about 40° C.; (2) preheat core tablets between 35–39° C.; (3) product temperature between about 25 to about 39° C.; and (4) final product temperature between about 35 to about 39° C. (in each case 1–4, a target, and particularly preferred temperature is about 35° C.).

In the preparation of oral dosage forms containing BIRB 796, use may be made of a "common blend" approach in which several potencies of tablets are prepared using different weights of the same blend. The blend may be used to make a number of oral dosage forms including tablets, filled hard gelatin capsules (of different sizes and/or net fills), caplets, powder papers, cachets, granules, etc.

It has been discovered that BIRB 796 may lead to discoloration of a core tablet in which it is contained when that core tablet is exposed to light or heat. It has been found that such coloration can be prevented by coating the BIRB 796 core tablet in particular with a light/heat absorbing coating, preferably a water dispersible pharmaceutically-acceptable polymer, or incorporation of a light/heat absorbing material into the core tablet. Tablet coatings preferably comprise 2–3%, more preferably about 2.5%, by weight of the BIRB 796 tablet. Masking of the color change may also be used to create a pharmaceutically acceptable dosage form, as for example, mixing dry colorants (including yellow no. 10 iron oxide lake) into the formulation.

BIRB 796 has been found to be pharmaceutically compatible with a number of compounds including hydrous lactose monohydrate, beta-cyclodextrin, povidone, microcrystalline cellulose, pre-gelatinized starch, sodium starch glycolate, colloidal silicon dioxide, and magnesium stearate. A preferred tablet formulation of BIRB 796 includes a soluble granulation aid (such as lactose monohydrate), a binding agent, preferably a granulating binding agent (such as povidone) and/or dry binding agent (such as microcrystalline cellulose), one or more disintegrants (such as pre-gelatinized starch and sodium starch glycolate), a flow aid (such as colloidal silicon dioxide), and a lubricant (such as magnesium stearate). It is preferred in order to produce a BIRB 796 tablet with a pharmaceutically adequate dissolution rate and compaction profile that the soluble granulation aid(s) comprise between 40 to 50% of the tablet weight, the dry binding agent(s) comprise between 30 to 50% of the tablet weight, the disintegrant(s) comprise between 5–40% of the tablet weight, the flow aid(s) comprise between 0.25 to 1% of the tablet weight, and the lubricant(s) comprise between 0.5 to 1% of the tablet weight. Buffering agents may also be added (typically comprising less than 1% of the total tablet weight). Depending on the size and dimensions of the core tablet pharmaceutically useful tablets have been found to made from such compositions using compressional forces between about 0.5 KN to about 12 KN.

EXAMPLE 1

BIRB 796B Tablet Production

BIRB 796, lactose monohydrate, and povidone were dry mixed in a drum mixer for 5 minutes. The resulting dry mix was then granulated in a shear mixer with water. The wet granulation was then spread onto stainless steel trays and dried in an oven at 40–50° C. to an LOD of =2%. The dried granules were then milled through an 18 mesh (1 mm) screen in cone mill.

Microcrystalline cellulose, pre-gelatinized starch, sodium starch glycolate, and colloidal silicon dioxide were then screened through an 18 mesh (1 mm) screen into the milled granules and the resulting mixture mixed in a drum mixer for 12 minutes at approximately 30 rpm. Magnesium stearate, a lubricant, was then pre-blended with some of the mixed blend, screened through an 18 mesh screen and returned to the drum to be mixed an additional 4 minutes under the same conditions. The resulting blend was then tabletted using tablet tooling and adjusting the tablet weight for the appropriate potency. After the blend was compressed into core tablets, the tablets were film coated. Tablets were coated to a weight increase of 2–3%.

EXAMPLE 2

BIRB 796 Tablet Production

BIRB 796 was solubilized in a pH 2, phosphate buffer to prepare a spray solution. Lactose monohydrate and povidone K30 were mixed and heated with low fluidization in a small fluid bed granulator (Uniglatt). The drug solution was sprayed onto the mixed powders in the fluid bed granulator. A rinse solution of buffer followed by purified water was used to minimize drug loss. The granulation was dried in the same unit to an LOD of =2% (Mettler LJ16 tester).

The dried granules were then milled in a cone mill with an 18 mesh (1 mm) grate screen at low speed. Microcrystalline cellulose, pre-gelatinized starch, sodium starch glycolate, and colloidal silicon dioxide were then screened through an 18 mesh screen into the milled granules and the resultant mixture mixed in a drum mixer for approximately 12 minutes at 30 rpm. Magnesium stearate, a lubricant, was then pre-blended with some of the mixed blend, screened through an 18 mesh screen and returned to the drum to be mixed an additional 4 minutes under the same conditions. The blend was then tabletted, and coated to a weight increase of about 2 to about 3%.

Several blends may be prepared, one for the highest potency manufactured (300 mg), one "common blend" for the high potency dosages (20, 25, 50, 100 and 200 mg), one for the low potency 5 mg dosage, and one "common blend" for the lowest potencies manufactured (0.5, 1.25 and 2.5 mg). Tablets may be prepared from the respective common blend using tablet tooling and adjusting the tablet weight for the appropriate potency. After the blend is compressed into tablets, the tablets may be film coated. Tablets may be coated to a weight increase of about 2 to about 3%, preferably about 2.5%.

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety herein.

What is claimed is:

1. A method for coating a compression containing more than about 10% betacylcodextrin, said method comprising:
    obtaining a compression containing more than 10% beta-cyclodextrin;
    coating said compression with a polymeric material at a product temperature between about 25 to about 39° C. and an air inlet temperature between about 30 to about 40° C.

2. The method according to claim 1 wherein the product temperature is 35° C.

3. The method according to claim 1 wherein the beta-cyclodextrin is more than 40%.

4. The method according to claim 2 wherein the beta-cyclodextrin is more than 40%.

5. The method according to claim 1 wherein the compression is a tablet comprising granulated 1-(5-tert-butyl-2-p-tolyl-2H-pyrazol-3-yl)-3-[4-(2-morpholin-4-yl-ethoxy)-naphthalen-1-yl]-urea.

6. The method according to claim 4 wherein the compression is a tablet comprising granulated 1-(5-tert-butyl-2-p-tolyl-2H-pyrazol-3-yl)-3-[4-(2-morpholin-4-yl-ethoxy)-naphthalen-1-yl]-urea.

7. A method for coating a compression, said compression comprising:
    (a) between 0.1 to 35% by weight granulated 1-(5-tert-butyl-2-p-tolyl-2H-pyrazol-3-yl)-3-[4-(2-morpholin-4-yl-ethoxy)-naphthalen-1-yl]-urea;
    (b) between 25 to 50% by weight binding agent;
    (c) between 3 to 40% by weight disintegrant; and
    (d) between 25 to 60% by weight soluble granulation aid;
    said method comprising coating said compression with a polymeric material at a temperature below 40° C.

8. The process according to claim 7 wherein the soluble granulation aid is lactose.

9. The process according to claim 7 wherein the soluble granulation aid is beta-cyclodextrin.

10. The process according to claim 7 wherein the granulated 1-(5-tert-butyl-2-p-tolyl-2H-pyrazol-3-yl)-3-[4-(2-morpholin-4-yl-ethoxy)-naphthalen-1-yl]-urea contains granules dimensioned such that the portion of granules which do not pass through a 1000 micron sieve do not account for more than about 5 percent by weight of the granules, the portion of granules that do not pass through a 250 micron sieve does not account for more than about 60 percent by weight, and the portion of granules that pass through a 63 micron sieve do not account for more than 20 percent by weight.

11. A pharmaceutical dosage form comprising a core compression comprising at least about 40% betacyclodextrin and a water-soluble polymeric coating substantially covering said core compression wherein said core compression is coated by the process of claim 1.

12. A pharmaceutical dosage form comprising a core compression comprising at least about 40% betacyclodextrin and a water-soluble polymeric coating substantially covering said core compression wherein said core compression is coated by the process of claim 7.

* * * * *